United States Patent [19]
Leonard et al.

[11] Patent Number: 5,937,140
[45] Date of Patent: Aug. 10, 1999

[54] THERMAL-FUSE PLUG-THROUGH, PLUG-IN DIFFUSER

[75] Inventors: Stephen B. Leonard; James R. Crapser, both of Caledonia, Wis.; Jeffrey A. Steininger, Fort Wayne, Ind.

[73] Assignee: S. C. Johnson & Son, Inc., Racine, Wis.

[21] Appl. No.: 08/716,722

[22] Filed: Sep. 23, 1996

[51] Int. Cl.$^6$ .......................... A61M 16/00; H01R 13/68; H01H 85/02
[52] U.S. Cl. .......................... 392/392; 439/622; 337/197
[58] Field of Search .................................. 392/390, 391, 392/392; 439/622, 623, 651, 373, 374, 375; 337/186, 187, 197, 198

[56] References Cited

U.S. PATENT DOCUMENTS

| | | | |
|---|---|---|---|
| 2,676,223 | 4/1954 | Whitaker | 439/622 |
| 2,683,201 | 7/1954 | Miller et al. | |
| 4,032,877 | 6/1977 | McAlister | 337/148 |
| 4,275,374 | 6/1981 | Chaucer | 337/197 |
| 4,307,925 | 12/1981 | Drew | 339/147 P |
| 4,309,068 | 1/1982 | Ahroni | 339/147 P |
| 4,758,184 | 7/1988 | Call | 439/622 |
| 4,804,821 | 2/1989 | Glucksman | 392/392 |
| 4,904,976 | 2/1990 | Liaq | 337/197 |
| 5,213,523 | 5/1993 | Hygema et al. | 439/620 |
| 5,451,173 | 9/1995 | Mai | 439/622 |
| 5,521,357 | 5/1996 | Lock et al. | 392/390 |
| 5,556,192 | 9/1996 | Wang | 392/390 |
| 5,647,053 | 7/1997 | Schroeder et al. | 392/390 |

FOREIGN PATENT DOCUMENTS

| | | |
|---|---|---|
| 0 686 988 A1 | 12/1995 | European Pat. Off. |
| 2 239 801 | 7/1991 | United Kingdom . |
| 2 275 609 | 9/1994 | United Kingdom . |
| 93/05821 | 4/1993 | WIPO . |

OTHER PUBLICATIONS

Technical Bulletin TCO–A, "Application and Installation of MICROTEMP® Thermal Cutoffs", Therm–O–Disc, Incorporated (Jun. 1993).

M. McQuade, "Proper Selection and Installation of Thermal Cutoff Devices," *Electrical Manufacturing* (Sep. 1998), pp. 29–31.

*Primary Examiner*—Teresa Walberg
*Assistant Examiner*—Sam Paik

[57] ABSTRACT

A plug-in diffuser, for use with a substance to be thermally diffused, includes first and second electrical assemblies, each including a male terminal and a female terminal electrically connected to the male terminal. A thermal cutoff mechanism switches from a conductive state to a non-conductive state at a threshold temperature. The male and female terminals of at least one of the terminal assemblies is electrically connected through the thermal cutoff mechanism. A receptacle holds the substance, and a heating element is connected between the first and second terminal assemblies for heating the substance held in the receptacle when the diffuser is plugged into an electrical outlet via the male terminals. The female terminals cooperate to form an electrical socket into which an external device can be plugged.

25 Claims, 8 Drawing Sheets

THERMAL-FUSE PLUG-THROUGH, PLUG-IN DIFFUSER

BACKGROUND OF THE INVENTION

1. Field of the Invention

The present invention relates to a plug-in thermal diffuser for use with a substance to be thermally diffused, and more particularly to a plug-in device which provides a plug-through electrical connector and a thermal cutoff to neutralize the device in the event of overheating.

2. Description of the Related Art

Plug-in diffusers are well known in the art. In these devices, a resistance heater is disposed in a housing, out of which electrical prongs extend directly. When the prongs are plugged into a wall socket, the resistance heater generates heat. A substance, such as fragrance or an insect repellant, to be emitted into the air is maintained, either in liquid or solid form, in close proximity to the heater. As the heater heats the substance, controlled amounts are vaporized and emitted into the surrounding atmosphere.

These devices are particularly well suited to domestic use, especially in rooms such as kitchens and bathrooms, because they provide a continuous, controlled flow of desired substance into the air. However, these devices do require the use of a wall outlet, which are often in short supply in the rooms to which they are so well suited.

Also well-known in the art are plug-through electrical connectors such as adapters or extension cords having a conventional plug/socket construction. In these connectors, connector sockets are provided into which the prongs of an external plug are inserted, and connector prongs are provided for insertion into a wall socket. The connector provides an electrical "bridge" by which an external device to which the external plug is attached is electrically connected to the wall outlet circuitry. These connectors are used in wall-type outlets from AC power sources, as well as with various other power supplies, as an interface between integrated circuits, as adapters for use with any of the above, and in many other applications.

What has not been proposed in the art is a plug-in diffuser which includes a plug-through electrical connector. This combination device would permit the plug-in diffuser to be used without sacrificing a wall outlet, because an external plug could be connected to the wall outlet circuitry through the device itself.

A potential hazard with both the plug-in diffusers and the plug-through connector devices is the danger presented by faulty wiring or poor plug connections. These may result in increased temperatures, plastic deformation, or a fire. Attempts have been made to address problems associated with such wiring or connection problems by providing a thermal fuse mechanism which will cut off current flow in the event that the temperature of or current through a particular portion of a device rises above a certain threshold level.

For instance, U.S. Pat. No. 4,032,877, "Protector For Electric Circuits" to McAlister, discloses a temperature control protector. Disposed at either end of a tubular casing 12 of the protector is a ferrule-type metal terminal 14, 20 with an opening 18, 22. A cylindrical eyelet 24 extends into casing 12 from opening 22. An elongated current-conducting member 30 extends into the opening 18 of terminal 14 and fits into an opening 25 in the inner end of eyelet 24. Masses of heat-softenable alloy 38, 40 mechanically secure and electrically bond the ends of the current-conducting member 30 to the terminal 14 and the eyelet 24, respectively. If the temperature of the protector 10 rises above the softening temperature of the masses 38, 40, a helical compression spring moves the current conducting member 30 to open the circuit, and moves the head 32 thereof to a position indicating an open circuit. However, the protector in the '877 patent is not specifically designed for use with a plug-type device.

On the other hand, U.S. Pat. No. 4,275,374, "Fuse-Plug Adapter For Electrical Cord" to Chaucer, discusses a plug that includes a removable electrical fuse (not disclosed as being thermally triggered), in which a male element 1 extends from bottom opening 11a'' toward a female element which is mounted in a first channel adjacent upper opening 11a'. Likewise, a male element 2 extends from an opening 11b'' of a second channel, and a female element corresponding, but not continuous, thereto is located adjacent upper opening 11b'. The male element 2 and its corresponding female element each have a flange extending into the third channel. The male and female flanges contact, respectively, a lower fuse contact 12a and an upper fuse contact 12b of an electrical fuse 12. The fuse 12 is insertable and removable from the third channel through an insertion hole 6 at the bottom end face of the housing structure.

Neither of the foregoing devices provides a plug-in diffuser for use with a substance to be thermally diffused, and nothing in the art discloses or suggests such a plug-in diffuser which provides a plug-through mechanism whereby a separate appliance can be used in the same electrical outlet.

Also, none provides a mechanism for such a plug-through, plug-in diffuser whereby the full electrical current is neutralized in the event of overheating.

In addition, none provide any exterior manifestation of overheating in the event the current is neutralized by the thermal cutoff mechanism.

Accordingly, there is a need in the art for a plug-in diffuser for use with a substance to be thermally diffused, which provides a mechanism through which an external device can be plugged into the same electrical outlet.

There is also a need in the art for such a plug-in diffuser which interrupts the flow of electric current through the device using a thermal cutoff mechanism in the event of overheating.

There is an additional need for such a plug-in diffuser which will physically manifest the overheating in the event the thermal cutoff mechanism interrupts the flow of electrical current.

SUMMARY OF THE INVENTION

An object of the invention is to address the foregoing needs in the art and to provide a plug-in diffuser, for use with a substance to be thermally diffused, having a mechanism whereby an external appliance can be plugged into the same electrical outlet.

An additional object of the invention is to provide such a device with a thermal cutoff mechanism to interrupt the flow of electrical current through the device in the event of overheating.

A further object of the invention is to provide such a plug-in diffuser which physically manifests the overheating in the event the thermal cutoff mechanism interrupts the flow of electricity through the device in response to that overheating.

In one aspect of the present invention, the plug-in diffuser, for use with a substance to be thermally diffused, includes first and second electrical terminal assemblies, each including a male terminal and a female terminal electrically connected to the male terminal. A thermal cutoff mechanism is provided which switches from a conductive state to a non-conductive state at a threshold temperature, the male and female terminals of at least one of the terminal assemblies being electrically connected to the thermal cutoff mechanism. A receptacle is provided for holding the substance, and the heating element is connected between the first and second terminal assemblies for heating the substance held in the receptacle when the diffuser is plugged into an electrical outlet via the male terminals.

This aspect of the present invention can include a thermally conductive, electrically-insulated subassembly encasing a thermal cutoff mechanism, and a main housing encasing the first and second terminal assemblies, the subassembly, and the thermal cutoff mechanism, with the male terminals extending out from the main housing and the female terminals being accessible through the main housing.

The main housing can be formed of a material that slightly deforms at approximately the threshold temperature. The portion of the main housing through which the male terminals extend can materially deform at approximately the threshold temperature. In a preferred embodiment, the main housing can be formed of polypropylene, and the threshold temperature can be within a range of approximately 95° C. to 105° C.

The heating element can be a resistance heating wire, and a heating plate can be provided disposed within the main housing into which the heating wire is embedded. The receptacle can be configured to receive a cartridge containing the substance, and the receptacle can hold the substance proximal to the face of the heating plate.

In a preferred embodiment, the female terminals cooperate to form an electrical socket into which an external electrical device can be plugged.

In another aspect of the present invention, a plug-in diffuser, for use with a substance to be thermally diffused, can include an outer casing defining a receptacle for holding the substance. An electrically-insulative first stage main body is encased within the outer casing, and a thermally conductive, electrically-insulated subassembly housing is encased within the main housing and interfitted with the first stage main body. A first terminal assembly can be provided, including a male terminal extending from the first stage main body and from the outer casing, and a first female terminal encased within the first stage main body and being electrically connected to the first male terminal. A second female terminal is encased in the first stage main body. A second male terminal extends from the subassembly housing and from the outer casing. A heating element, for heating the substance held in the receptacle when the diffuser is plugged into an outlet via the male terminals, is disposed in the first stage main body and electrically connected between the first terminal assembly and the second female terminal. A thermal cutoff mechanism is provided which switches from the conductive state to a non-conductive state at a threshold temperature. The thermal cutoff mechanism has two lead terminals, one lead terminal being electrically connected to a second male terminal, and another lead terminal being electrically connected to a second female terminal when the subassembly housing is interfitted with the first stage main body.

In yet another aspect of the present invention, a plug-in diffuser, for use with a cartridge of substance to be thermally diffused, includes a polypropylene outer casing defining a receptacle for holding the cartridge. An electrically insulative first stage main body is encased within the outer casing. A thermally conductive, electrically-insulative subassembly housing is encased within the main housing and is interfitted with a first stage main body.

A first terminal assembly is provided, which includes a first male terminal extending from the first stage main body and from the outer casing, and a first female terminal encased within the first stage main body and electrically connected to the first male terminal. A second female terminal is encased within the first stage main body. A second male terminal extends from the subassembly housing and from the outer casing.

A resistance heating wire is provided for heating the substance held in the receptacle when the diffuser is plugged into an electrical outlet via the male terminals. The heating wire is electrically connected between the first terminal assembly and the second female terminal. A heating plate is disposed within the main housing with the heating wire embedded therein. The receptacle holds the cartridge proximal to a face of the heating plate.

A thermal cutoff mechanism is provided which switches from the conductive state to a non-conductive state at a threshold temperature. The thermal cutoff mechanism has two lead terminals, one of which is electrically connected to a second male terminal and another of which is electrically connected to the second female terminal when the subassembly housing is interfitted with the first stage main body. A portion of the main housing through which the male terminals extend materially deforms at approximately the threshold temperature.

This brief summary of the invention has been provided so that the nature of the invention may be generally understood. However, this summary should not be construed to limit the invention.

The foregoing and other objects, aspects, features, and advantages of the present invention will become apparent from the following detailed description of the preferred embodiments in conjunction with the accompanying drawings.

BRIEF DESCRIPTION OF THE DRAWINGS

Like reference numerals have been used throughout the views for like or corresponding elements.

DETAILED DESCRIPTION OF PREFERRED EMBODIMENTS

Figure 1A:
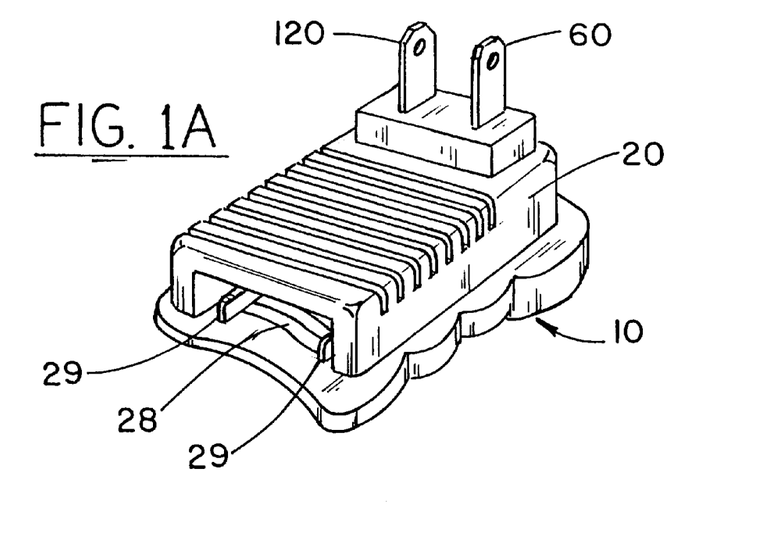
FIG. 1A is a perspective view of an embodiment of the plug-in diffuser of the present invention.
Figure 1B:
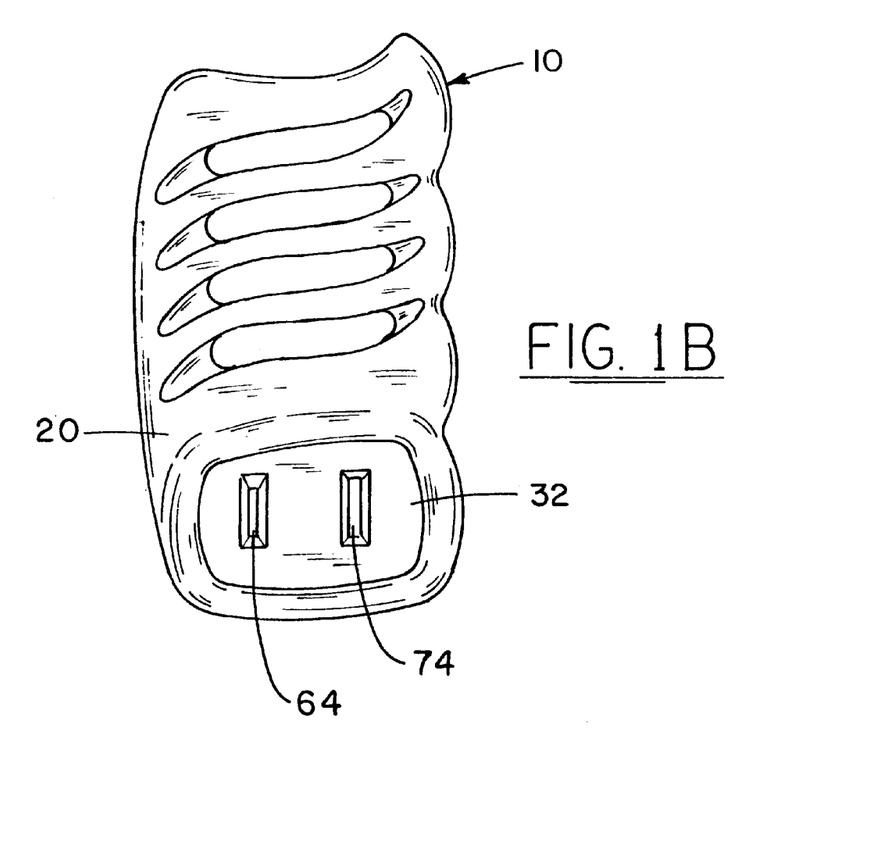
FIG. 1B is an elevational, plan view of an embodiment of the plug-in diffuser of the present invention.

FIGS. 1A and 1B show the plug-in diffuser 10 of the preferred embodiment of the present invention. FIG. 1A, a perspective view, shows a pair of electrical prongs 60, 120 extending from an outer casing 20. A slot 28 is provided to receive, for example, a specially-adapted fragrance or insect repellent cartridge (not shown). Within the slot 28 are rails 29, which engage protrusions on the cartridge to guide the cartridge during insertion and hold the cartridge in position. With the cartridge inserted into the slot 28, the unit is plugged into an electrical outlet via the pair of electrical prongs 60, 120. Once plugged in, the unit heats the fragrance cartridge, for example, releasing fragrance into the atmosphere. Once the fragrance cartridge is spent, it can be removed and replaced.

It should be noted that the present invention is not limited to use with these specially-designed fragrance cartridges. For instance, the present invention can be designed as a container that holds any suitable liquid substance, such as a fragrance or an insect repellent, to be heated and emitted. Alternatively, a port could be provided to which separately provided containers could be attached.

Turning to FIG. 1B, an elevational plan view of the front of the diffuser 10, a pair of sockets 64, 74 are provided into which an external electrical device can be plugged to access the electrical outlet through the diffuser 10. Thus, when the diffuser 10 is plugged into an outlet and being used to emit fragrance, for example, the outlet into which it is plugged can still be accessed for use by another appliance, maximizing outlet availability. In use, the diffuser 10 is designed to accept all non-grounded plugs and is used in the same manner as a typical plug adapter. A snap-on front female plug plate 32 which snaps into the outer casing 20 as shown, defines the sockets 64, 74.

Enclosed within the outer casing 20 are all of the internal components of the diffuser 10, including a thermal cutoff device ("TCO") (described later in more detail) that neutralizes the diffuser 10 in the event of overheating. If heat is generated in the diffuser 10 by a high resistance connection, a faulty wiring, or the like, the TCO is designed to "open" and neutralize the diffuser 10 by cutting off electricity through the device. This also cuts off the current from the wall socket to the external appliance which is plugged in through the diffuser 10.

The internal components of the diffuser 10 will now be described with reference to FIG. 2, which shows an exploded, perspective view. To facilitate manufacturing, the components are initially assembled into a first stage 50 and a subassembly 100 which are fit together during the final stages of assembly, as discussed later with respect to FIG. 8. The first stage 50, the assembly of which will be described later, includes a housing 51. The housing 51 includes a heating plate 55, which is a flat projection with a heating wire embedded therein. Also included in the first stage 50 are a first male terminal ("prong") 60 and a first female terminal ("socket") 63 which are unitarily formed into a single terminal assembly 65. Also provided in the first stage is a second female terminal 73. When the first stage is assembled, as shown later, the heating wire is connected to the second female terminal 73 at crimp 75 and to the terminal assembly 65 at crimp 67. The second female terminal 73, the terminal assembly 65, and the heating wire are then all molded into the housing 51.

The subassembly 100, the assembly of which is described below, includes a thermally conductive sheath 96, a second male terminal 120 and a thermal cutoff mechanism 94. The second male terminal 120 inserts into the opening 96a of the sheath 96. Lead line 94a of the thermal cutoff mechanism 94 connects to the second male terminal within the sheath 96. When the subassembly is interfitted with the first stage 50, as discussed later, a lead line 96b of the thermal cutoff mechanism 94 electrically connects with the second female terminal 73 at a contact face 77, which completes the connection between the second male and female terminals 120, 73.

Figure 2:
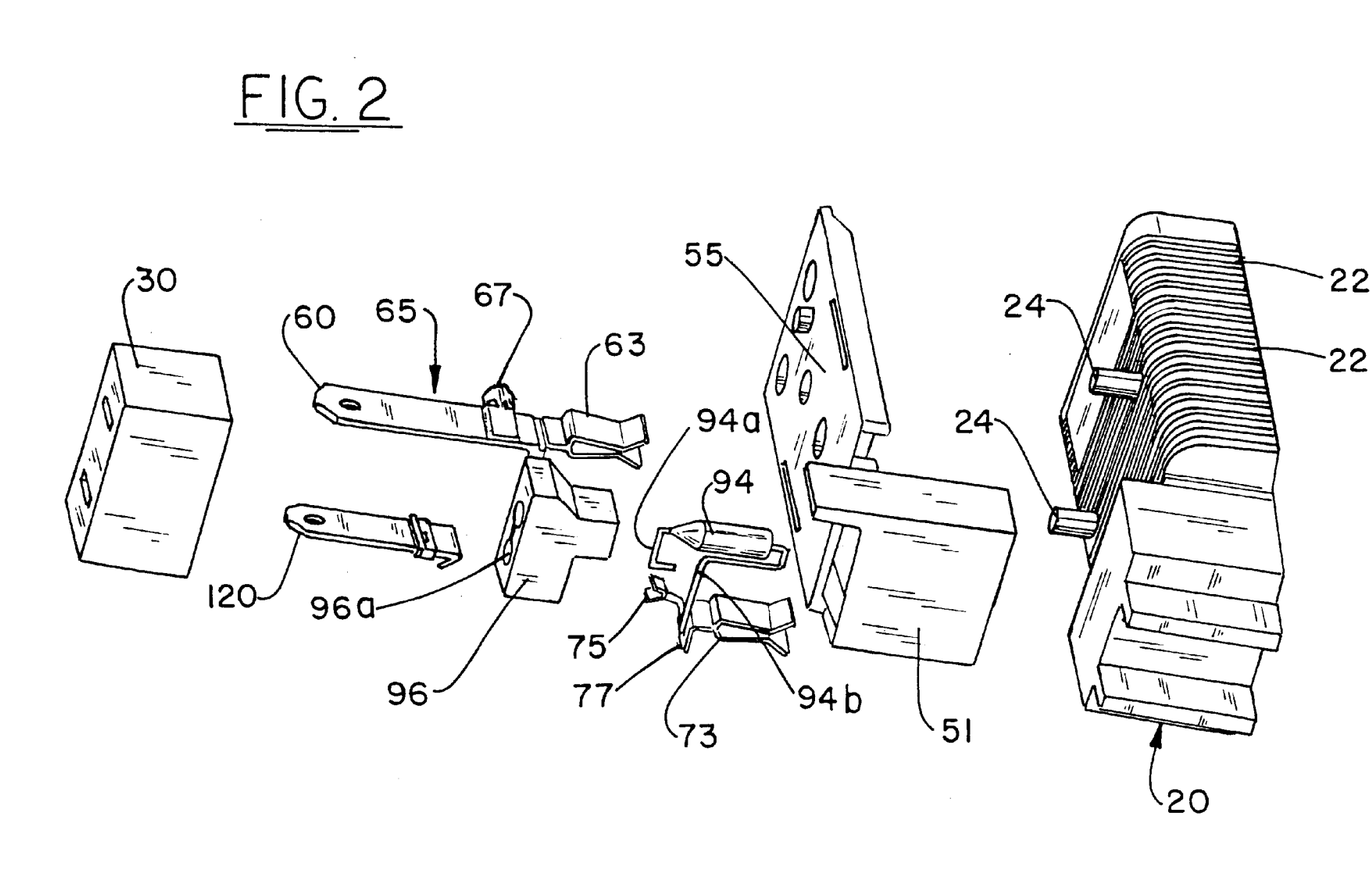
FIG. 2 is an exploded perspective view of the plug-in diffuser of the present invention.

Also shown in FIG. 2 is a terminal containment cap 30, which encases the subassembly 100 and a portion of the first stage 50 when they are interfitted, as discussed later, and the second stage overmold outer casing 20, which encases all of the components once assembled. Ribs 22 are disposed on the outer casing to aid in the dissipation of heat from the diffuser 10. Stand-offs 24 project from the face of the outer casing to engage the wall when the diffuser 10 is plugged into an outlet, thereby reducing "rocking" within the outlet. The thermal containment cap 30 and the outer casing 20 are both formed of polypropylene or some other suitable plastic having appropriate thermal properties, as discussed later.

Figure 3:
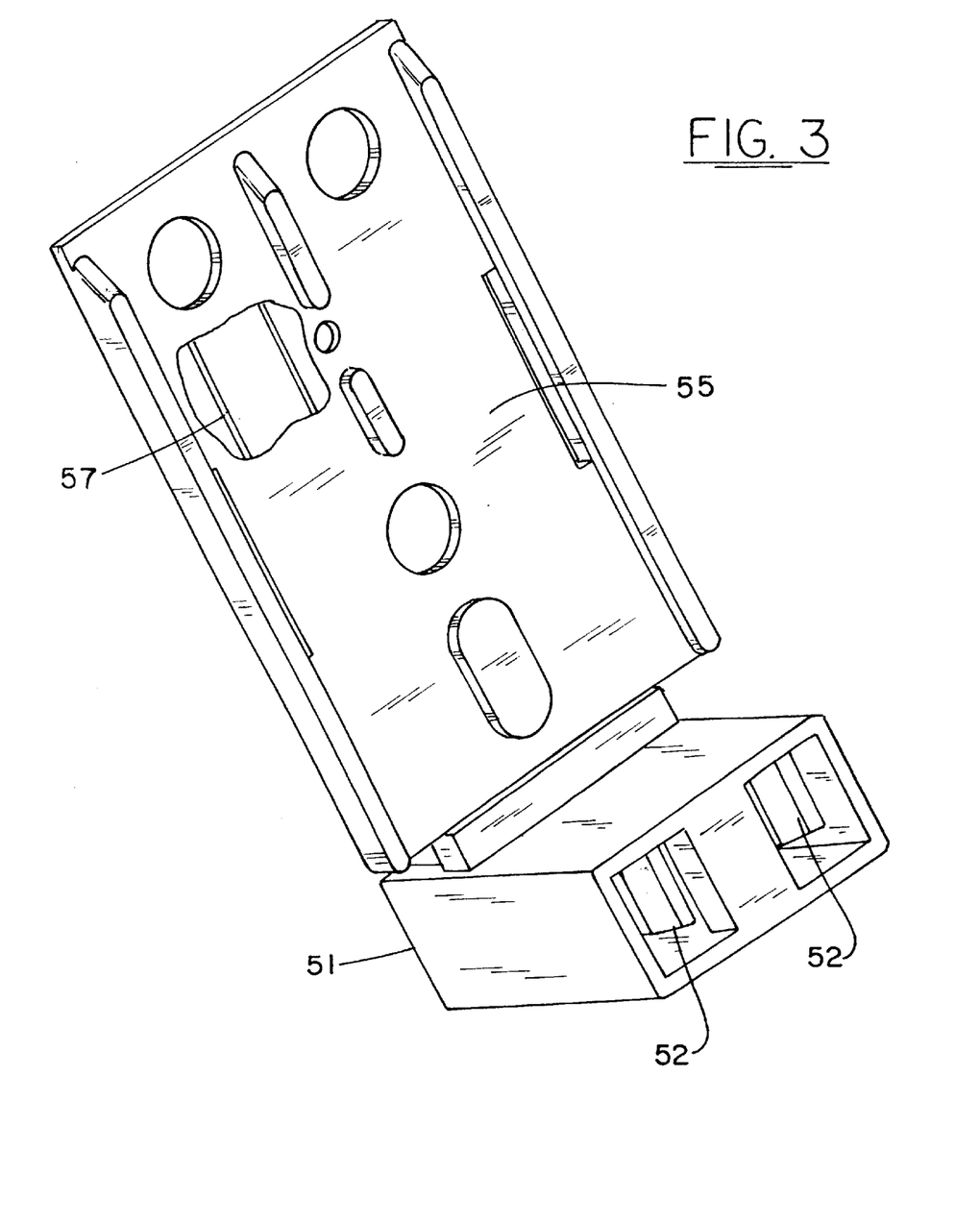
FIG. 3 is a partial cut-away perspective view of a first stage housing component shown in FIG. 2.

FIG. 3 shows a partial cut-away, perspective view of the housing 51 of the first stage 50, which is molded in one piece of polypropylene or other appropriate thermally resistant plastic. A heating wire 57 is embedded within the heating plate 55, snaking back and forth just below the surface of the heating plate 55 to provide a relatively uniform heating surface. Openings 52 are provided in the housing for access to the first and second female terminals, which are embedded within the housing 51.

Figure 4:
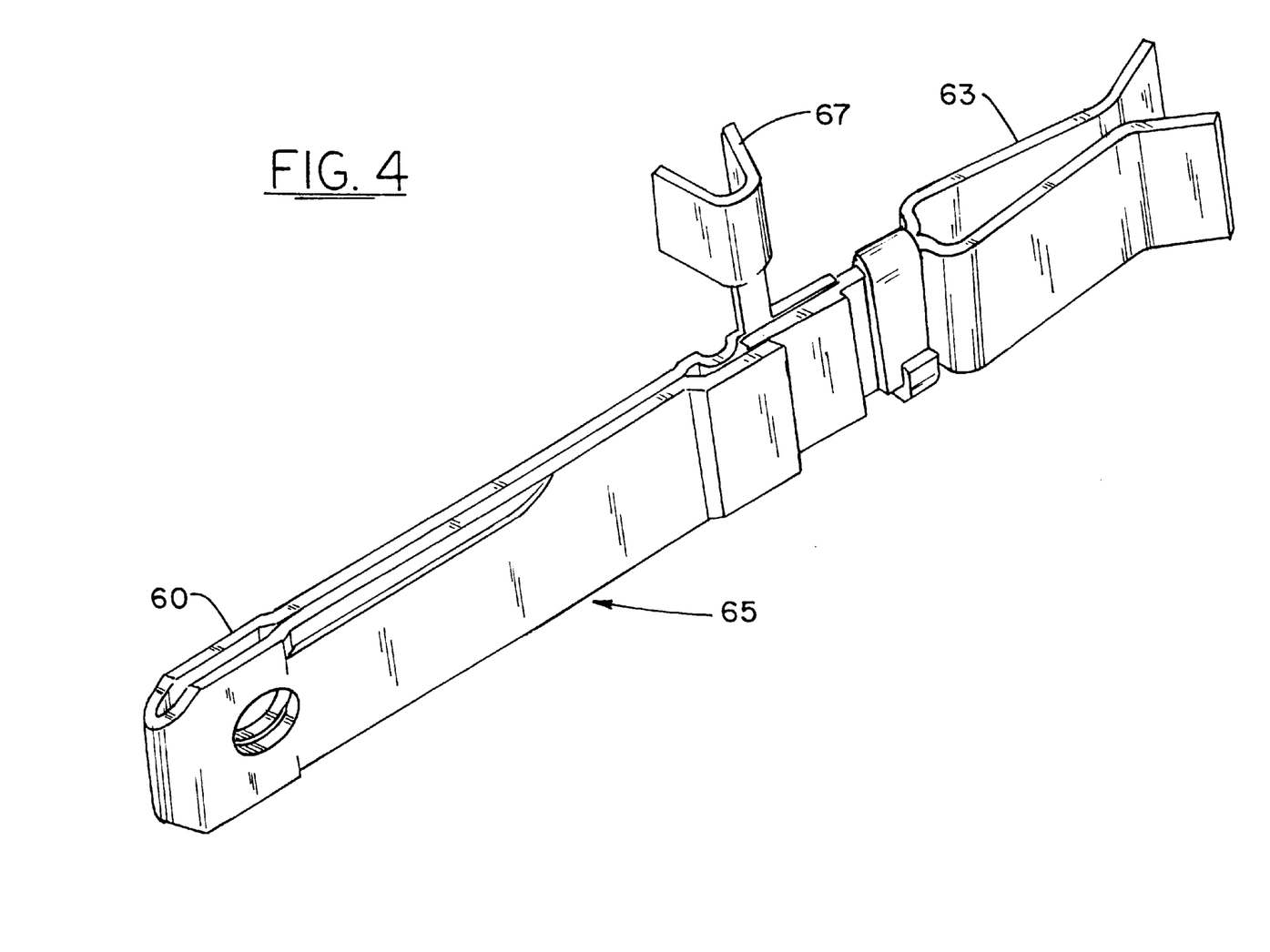
FIG. 4 is a perspective view of the terminal assembly component shown in FIG. 2.

FIG. 4 shows a perspective view of the terminal assembly 65. The first female and male terminals 63, 60 are disposed at either end of the terminal assembly 65. The crimp 67 is provided to connect the terminal assembly 65 to the heating wire. The heating wire 57 is inserted into the U-shaped opening of the crimp 67, which is closed around the heating wire 57.

Figure 5:
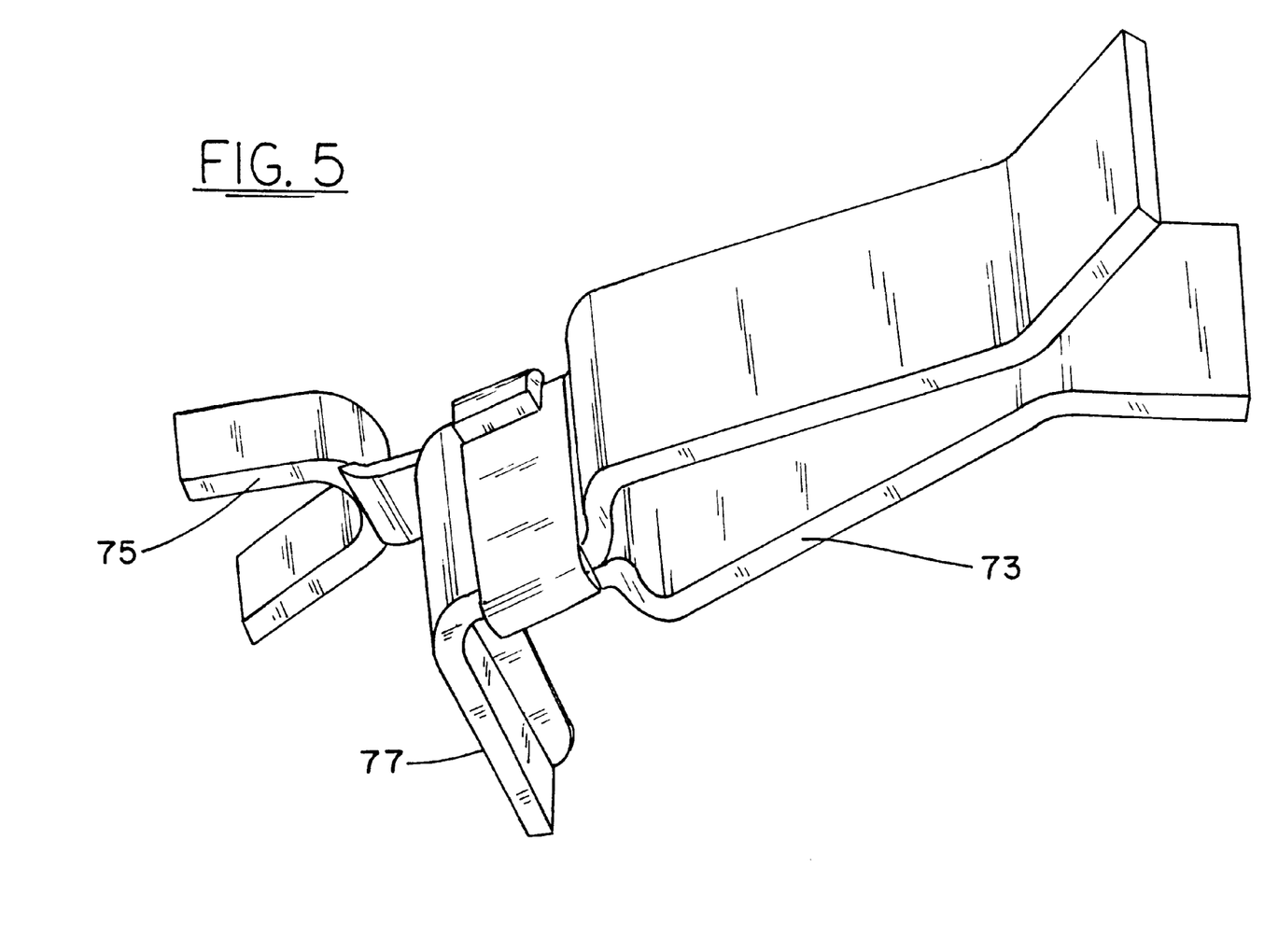
FIG. 5 is a perspective view of the female terminal component shown in FIG. 2.

FIG. 5 shows a perspective view of the second female terminal 73, which also has a crimp 75 for similar connection to the heating wire 57. Also, the contact face 77 is provided for engagement with the thermal cutoff mechanism 94 when the subassembly 100 is fitted together with the first stage 50.

Figure 6:
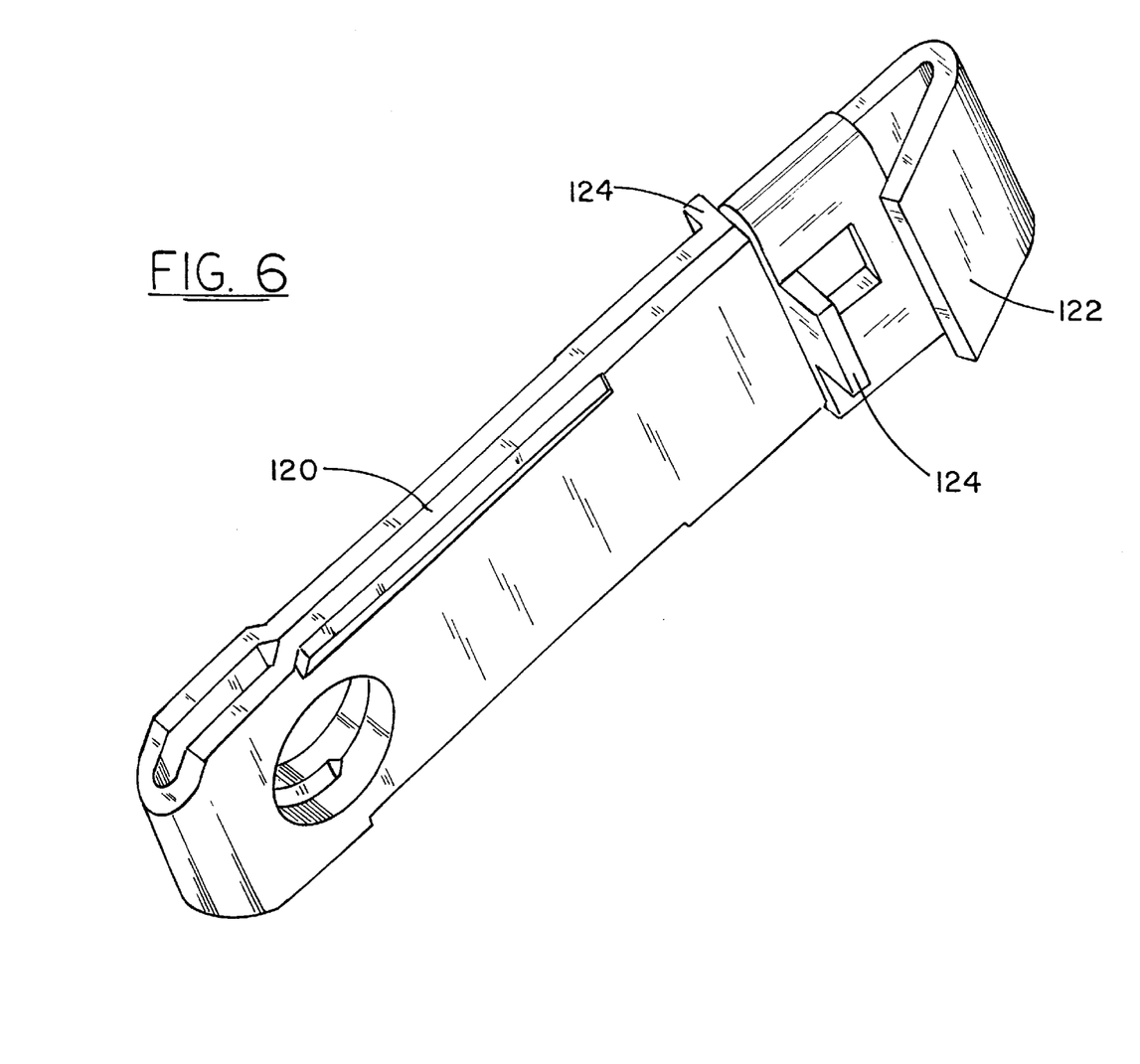
FIG. 6 is a perspective view of a male terminal component illustrated in FIG. 2.

FIG. 6 shows a perspective view of the second male terminal 120. An engagement fold 122 is provided at its proximal end for engagement with the line 94a of the thermal cutoff mechanism 94. The lead line 94a is inserted into the fold 122. When the second male terminal 120 is inserted into the sheath 96, the engagement fold 122 is forced closed over the lead line 94a, securing the connection between the second male terminal 120 and the thermal cutoff mechanism 94. Guide projections 124 are provided as a guide during assembly of the second male terminal 120 into the sheath 96.

Figure 7A:
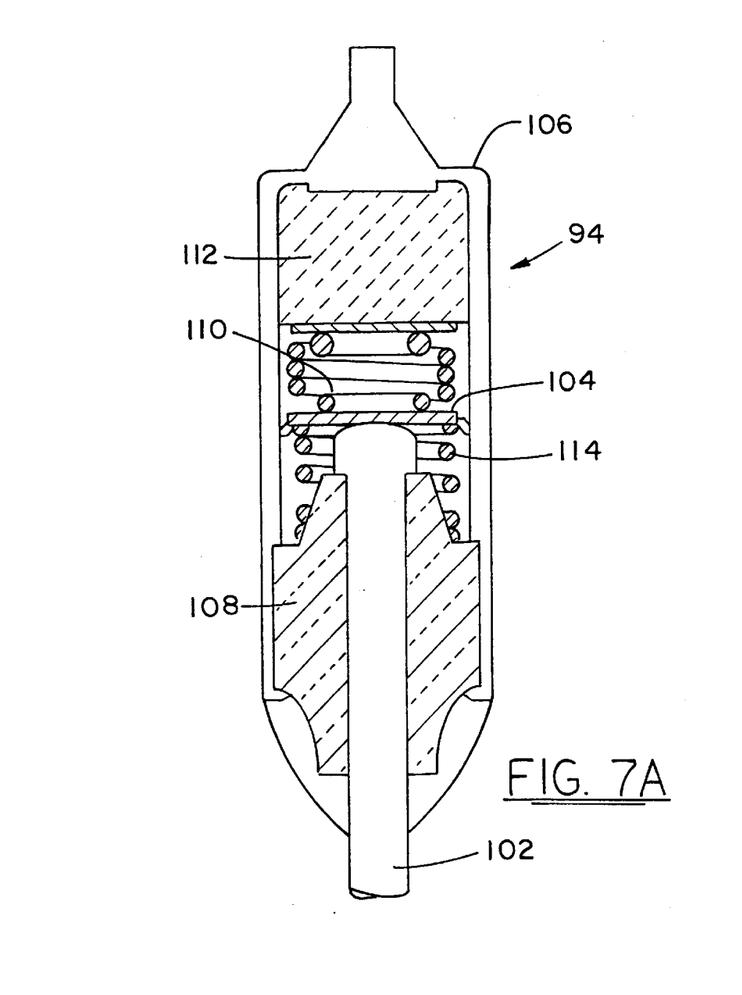
FIGS. 7A and 7B are partial cut-away plan views of the thermal cutoff component shown in FIG. 2.
Figure 7B:
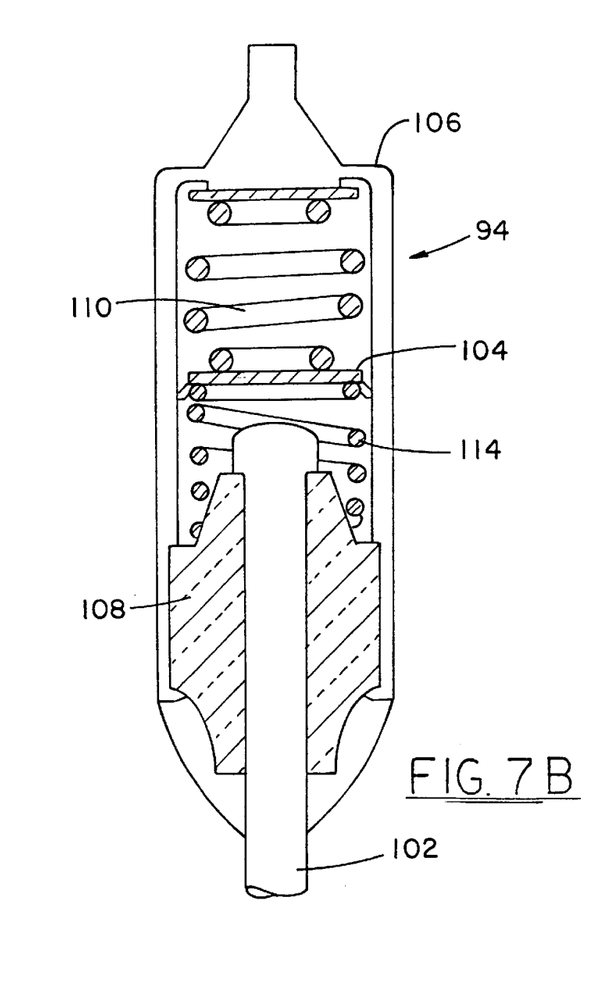

Turning to FIGS. 7A and 7B, thermal cutoff mechanisms are available in a variety of configurations, and the particular configuration utilized is not essential to the present invention. However, thermal cutoffs commercially available under the trademark MICROTEMP® from Therm-O-Disc, Inc., Mansfield, Ohio, have proven to be well suited for this application. The details of a thermal cutoff mechanism having this general configuration will now be discussed with reference to FIGS. 7A and 7B. Referring to FIG. 7A, the thermal cutoff mechanism 94 includes a multi-staged conductive element made up of pin contact 102, movable contact 104, and lead assembly 106. Pin contact 102 is held in place and out of contact with lead assembly 106 by bushing 108. Movable contact 104 is slidably disposed in contact with lead assembly 106, and is urged against pin contact 102 by compression spring 110, which is disposed between movable contact 104 and thermal seat 112. Current passes between pin contact 102 and lead assembly 106 via movable contact 104.

The thermal seat 112 is made up of an electrically non-conductive material which melts at a threshold temperature. This threshold temperature can be set or varied, as desired. Typical threshold temperatures are on the order of 75° C. to 215° C. If the thermal cutoff mechanism 94 exceeds this threshold temperature, the seat 112 will melt, allowing the compression spring 110 to expand as shown in FIG. 7B. When compression spring 110 expands, the force with which it urges movable contact 104 against pin contact 102 decreases. This reduction in urging force allows trigger spring 114 to expand and force the movable contact 104 away from pin contact 102, as shown in FIG. 7B. Thus, the conductive element 92 is opened, disrupting the flow of current through thermal cutoff mechanism 94.

For a more detailed discussion of the MICROTEMP® thermal cutoffs, the disclosures of Therm-O-Disc, Inc.'s *Technical Bulletin TCO-A* and Michael McQuade's article entitled "Proper Selection and Installation of Thermal Cutoff Devices" in *Electrical Manufacturing* (September 1988), pages 29–31, are incorporated herein by reference.

The sheath 96 (not shown in this figure) which encases the thermal cutoff mechanism 94 should be electrically non-conductive while thermally conductive. While any of a number of materials fit these specifications, a compound commercially marketed by Phillips Petroleum Company under the trademark RYTON® has proven to be particularly well suited for this use because of its thermal conductivity and hardness. Of course, other materials, which perform equivalent functions also could be used, such as ABS (acrylonitrile butadiene styrene), polystyrene and high-density polyethylene.

Figure 8:
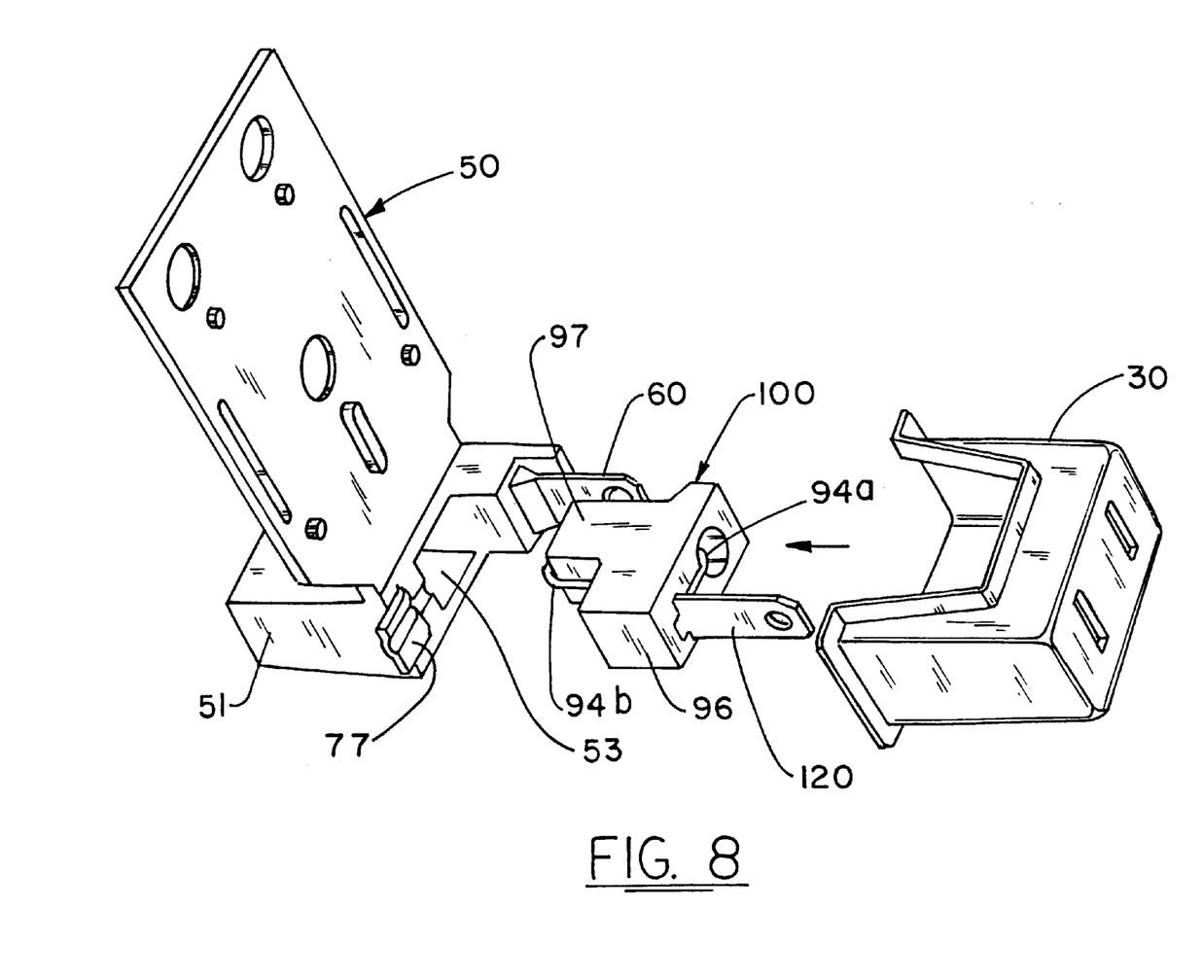
FIG. 8 is a partially exploded, perspective view of an embodiment of the plug-in diffuser of the present invention.

FIG. 8 illustrates the assembly of the major internal components of the diffuser 10. In this figure, the first stage 50 has been assembled. The first male terminal 60 extends out from the first stage housing 51. The contact face 77 of the second female terminal 73 (embedded within the first stage housing 51) is exposed. A cavity 53 is provided to receive the subassembly 100.

The second male terminal 120 extends out from the subassembly 100. The lead line 94a connects the thermal cutoff mechanism 94 (embedded within the sheath 96) to the second male terminal 120. An insertion tab 97 of the sheath 96 fits into the cavity 53 of the first stage 50. The lead line 94b engages the contact face 77 of the second female terminal 73 when the insertion tab 97 is inserted into the cavity 53.

Once the subassembly 100 and the first stage 50 are assembled together, the terminal containment cap 30 fits over them.

The particular properties of the thermal cutoff mechanism 94 and the outer casing of the diffuser are selected so that the plastic of the outer casing, preferably around the male terminals, will deform to a desired degree in the event of overheating. The amount of deformation can be varied as desired based on the operating temperatures and selection of materials, for example. Nevertheless, we prefer that this deformation be a plastic, and not an elastic, deformation. Therefore, when the thermal cutoff mechanism 94 neutralizes the diffuser, the outer casing will have deformed to a desired degree, providing a visual indication that overheating has occurred. As discussed earlier, the thermal cutoff rating can be adjusted within a wide temperature range. The relative temperature index ("RTI") of the material of the outer casing, the temperature at which pre-melt softening will occur, is selected in conjunction with the TCO rating to provide optimal performance. The housing of the first stage needs to have a high enough RTI to withstand prolonged exposure to the heating elements, preferably on the order of 90° C. to 130° C. In addition, the TCO rating and the relative temperature index of the outer casing must be selected within appropriate ranges to be compatible with the over-molding process during assembly. In the preferred embodiment, the TCO rating is in the 95° C. to 105° C. range, and the relative temperature index of the outer casing is approximately 100° C. to 120° C. Finally, the outer casing, as well as the internal terminal containment cap and the snap-on front female plug plate—are all constructed of V-0 grade material, which is flame retardant.

INDUSTRIAL APPLICABILITY

The plug-in diffuser electrical connector of the present invention can be used wherever it is desirable to provide a plug-in diffuser in which another device can be plugged into the wall outlet through the diffuser. The inclusion of the thermal cutoff mechanism makes the present invention useful wherever temperature control or fire hazard prevention is desired.

Although specific embodiments of the present invention have been described in detail, it will be understood that this description is merely for purposes of illustration. Various modifications of and equivalent structures corresponding to the disclosed aspects of the preferred embodiments in addition to those described above may be made by those skilled in the art without departing from the spirit of the following claims. Additionally, those of ordinary skill in the art will appreciate that certain variations in the size, shape, number, arrangement, and material of various portions of the disclosed diffuser may be made without departing from the spirit of the invention. Accordingly, the scope of the invention defined by the following claims should be accorded the broadest reasonable interpretation so as to encompass such modifications and equivalent structures.

What is claimed is:

1. A plug-in diffuser, for use with a substance to be thermally diffused, said diffuser comprising:

first and second electrical terminal assemblies, each comprising a male terminal and a female terminal electrically connected to said male terminal;

a thermal cutoff mechanism interposed in series between said male and female terminals of at least one of said terminal assemblies, said thermal cutoff mechanism switching from a conductive state to a non-conductive state, so as to interrupt current between said male and female terminals of said at least one terminal assembly, when exposed to a threshold temperature within a preselected range;

a receptacle for holding the substance; and a heating element connected between said first and second terminal assemblies for heating the substance held in the receptacle when said diffuser is plugged into an electrical outlet via said male terminals.

2. The plug-in diffuser of claim 1, further comprising:

a thermally-conductive, electrically-insulative subassembly encasing said thermal cutoff mechanism; and a main housing encasing said first and second terminal assemblies, said subassembly, and said thermal cutoff mechanism, with said male terminals extending out from said main housing and said female terminals being accessible through said main housing.

3. The plug-in diffuser of claim 2, wherein said main housing is comprised of a material that deforms at approximately the threshold temperature.

4. The plug-in diffuser of claim 3, wherein a portion of said main housing through which said male terminals extend materially deforms at approximately the threshold temperature.

5. The plug-in diffuser of claim 4, wherein said main housing is comprised of polypropylene.

6. The plug-in diffuser of claim 1, wherein the preselected range is about 95° C. to about 105° C.

7. The plug-in diffuser of claim 1, wherein said heating element comprises a resistance heating wire.

8. The plug-in diffuser of claim 7, further comprising a heating plate disposed within said main housing into which said heating wire is embedded.

9. The plug-in diffuser of claim 8, wherein said receptacle is configured to receive a cartridge containing the substance.

10. The plug-in diffuser of claim 9, wherein said receptacle holds the cartridge containing the substance proximal to a face of said heating plate.

11. The plug-in diffuser of claim 1, wherein said female terminals cooperate to form an electrical socket for receiving a plug of an external electrical device.

12. A plug-in diffuser, for use with a substance to be thermally diffused, said diffuser comprising:
    an outer casing defining a receptacle for holding the substance;
    an electrically-insulative first stage main body encased within said outer casing;
    a thermally-conductive, electrically-insulative subassembly housing encased within said main housing and interfitted with said first stage main body;
    a second female terminal encased in said first stage main body;
    a first terminal assembly comprising a first male terminal, extending from said first stage main body and from said outer casing, and a first female terminal, encased in said first stage main body and being electrically connected to said first male terminal;
    a second male terminal extending from said subassembly housing and from said outer casing;
    a heating element, for heating the substance held in the receptacle when said diffuser is plugged into an outlet via said male terminals, said heating element being disposed in said first stage main body and electrically connected between said first terminal assembly and said second female terminal; and
    a thermal cutoff mechanism, having two lead terminals, which switches from a conductive state, in which current flows between two lead terminals, to a non-conductive state, in which current does not flow between the two lead terminals, when exposed to a threshold temperature, said thermal cutoff mechanism being interposed in series between said second male terminal and said second female terminal so that one lead terminal is electrically connected to said second male terminal and another lead terminal is electrically connected to said second female terminal when said subassembly housing is interfitted with said first stage main body, so that exposure of said thermal cutoff mechanism to the threshold temperature interrupts current between said second male terminal and said second female terminal.

13. The plug-in diffuser of claim 12, wherein said main housing is comprised of a material that deforms at approximately the threshold temperature.

14. The plug-in diffuser of claim 13, wherein a portion of said main housing through which said male terminals extend materially deforms at approximately the threshold temperature.

15. the plug-in diffuser of claim 14, wherein said main housing is comprised of polypropylene.

16. The plug-in diffuser of claim 12, wherein the threshold temperature is within the range of about 95° C. to about 105° C.

17. The plug-in diffuser of claim 12, wherein said heating element comprises a resistance heating wire.

18. The plug-in diffuser of claim 17, further comprising a heating plate disposed within said main housing into which said heating wire is embedded.

19. The plug-in diffuser of claim 18, wherein the receptacle is configured to receive a cartridge containing the substance.

20. The plug-in diffuser of claim 19, wherein the receptacle holds the substance proximal to a face of said heating plate.

21. The plug-in diffuser of claim 12, wherein said female terminals cooperate to form an electrical socket for receiving a plug of an external electrical device.

22. The plug-in diffuser of claim 12, wherein the threshold temperature is within a preselected range.

23. A plug-in diffuser, for use with a cartridge of a substance to be thermally diffused, said diffuser comprising:
    a polypropylene outer casing defining a receptacle for holding the cartridge;
    an electrically-insulative first stage main body encased within said outer casing;
    a thermally-conductive, electrically-insulative subassembly housing encased within said main housing and being interfitted with said first stage main body;
    a first terminal assembly comprising a first male terminals, extending from said first stage main body and from said outer casing, and a first female terminal, encased in said first stage main body and being electrically connected to said first male terminal;
    a second female terminal encased in said first stage main body;
    a second male terminal extending from said subassembly housing and from said outer casing;
    a resistance heating wire, for heating the cartridge held in the receptacle when said diffuser is plugged into an electrical outlet via said male terminals, said heating wire being electrically connected between said first terminal assembly and said second female terminal;
    a heating plate disposed within said main housing, and into which said heating wire is embedded, wherein the receptacle holds the cartridge proximal to a face of said heating plate; and
    a thermal cutoff mechanism, having two lead terminals, which switches from a conductive state, in which current flows between the two lead terminals, to a non-conductive state, in which current does not flow between the two lead terminals, when exposed to a threshold temperature, said thermal cutoff mechanism being interposed in series between said second male terminal and said second female terminal so that one lead terminal is electrically connected to said second male terminal and another lead terminal is electrically connected to said second female terminal when said subassembly housing is interfitted with said first stage main body, so that exposure of said thermal cut-off mechanism to the threshold temperature interrupts current between said second male terminal and said second female terminal, wherein a portion of said main housing through which said male terminals extend materially deforms at approximately the threshold temperature, and wherein said female terminals cooperate to form an electrical socket for receiving a plug of an external electrical device.

24. The plug-in diffuser of claim 23, wherein the threshold temperature is within the range of about 95° C. to about 105° C.

25. The plug-in diffuser of claim 23, wherein the threshold temperature is within a preselected range.

* * * * *